US008544328B2

(12) United States Patent
Sohn et al.

(10) Patent No.: US 8,544,328 B2
(45) Date of Patent: Oct. 1, 2013

(54) TRANSDUCER BASED HEALTH MONITORING SYSTEM

(75) Inventors: Hoon Sohn, Seoul (KR); Chul Min Yeum, Cheongju (KR); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 48 days.

(21) Appl. No.: 13/083,957

(22) Filed: Apr. 11, 2011

(65) Prior Publication Data

US 2012/0255359 A1 Oct. 11, 2012

(51) Int. Cl.
*G01N 29/07* (2006.01)

(52) U.S. Cl.
USPC ............................................ 73/598; 73/602

(58) Field of Classification Search
USPC ................... 73/598, 579, 597, 602; 702/35, 702/36, 39, 159, 183–185, 188
See application file for complete search history.

(56) References Cited

U.S. PATENT DOCUMENTS

| | | | |
|---|---|---|---|
| 5,431,054 A | 7/1995 | Reeves et al. | |
| 5,563,346 A | 10/1996 | Bartelt et al. | |
| 6,996,480 B2* | 2/2006 | Giurgiutiu et al. | 702/35 |
| 7,286,964 B2* | 10/2007 | Kim | 702/183 |
| 7,333,898 B2* | 2/2008 | Griess et al. | 702/35 |
| 7,596,470 B2* | 9/2009 | Kim | 702/183 |
| 7,743,659 B2 | 6/2010 | Kearns et al. | |
| 7,822,573 B2* | 10/2010 | Ihn | 702/113 |
| 7,881,881 B2 | 2/2011 | Giurgiutiu et al. | |
| 7,917,311 B2 | 3/2011 | Finkel et al. | |
| 7,921,727 B2* | 4/2011 | Rice | 73/762 |
| 7,991,587 B2* | 8/2011 | Ihn | 702/183 |
| 8,286,490 B2 | 10/2012 | Ruzzene et al. | |
| 8,286,492 B2* | 10/2012 | Sohn et al. | 73/628 |
| 2007/0265808 A1* | 11/2007 | Kim | 702/188 |

FOREIGN PATENT DOCUMENTS

GB 2451959 * 2/2009

OTHER PUBLICATIONS

U.S. Appl. No. 13/084,276, filed Apr. 11, 2011, Sohn et al.
Petculescu et al., "Group delay measurements using modally selective Lamb wave transduceers for detection and sizing of delaminations in composites", Smart Materials and Structures, 17 (2008) pp. 1-9.
Sohn, "Effects of environmental and operational variability on structural health monitoring", Philosophical Transactions of the Royal Society, 2007, pp. 1-23.
Thomas et al., "Corrosion Damage Detection with Piezoelectric Wafer Active Sensors", SPIE's 11th Annual International Symposium on Smart Structures and Materials and 9th Annual International Symposium on NDE for Health Monitoring and Diagnostics, Mar. 2004, San Diego CA, paper #5394-2, pp. 1-13.

(Continued)

*Primary Examiner* — J M Saint Surin
(74) *Attorney, Agent, or Firm* — Yee & Associates, P.C.

(57) ABSTRACT

A method and apparatus for detecting an inconsistency in an object. A signal sent from a first transducer unit is received at a second transducer unit. The signal is sent along a path through an object from the first transducer unit to the second transducer unit. The second transducer unit has segments. A velocity is identified at each segment in the segments for a number of modes for the signal to form identified velocities. A determination is made as to whether the inconsistency is present along the path through the object using the identified velocities for the number of modes for the signal.

17 Claims, 7 Drawing Sheets

(56) References Cited

OTHER PUBLICATIONS

Sohn et al., "Statistical Damage Classification under Changing environmental and Operational Conditions", Journal of Intelligent Materials Systems and Structures, 1992, pp. 1-17.

Oh et al., "Damage diagnosis under environmental and operational variations using unsupervised support vector machine", Elsevier, Journal of Sound and Vibration, 2009, pp. 1-16.

Park et al., "Time Reversal Active Sensing for Health Monitoring of a Composite Plate", Journal of Sound and Vibration, 2004, pp. 1-33.

Yeum et al., "Lamb wave mode decomposition using concentric ring and circular piezoelectric transducers", Wave Motion (2011), pp. 1-13.

Kim et al., "Instantaneous reference-free crack detection based on polarization characteristics of piezoelectric materials", Smart Materials and Structures, 2007, pp. 2375-2387.

Wooh et al., "Synthetic Phase Tuning of Guided Waves", IEEE Transactions on Ultrasonics, Ferroelectrics, and Frequency Control, vol. 48 No. 1, Jan. 2001, pp. 209-223.

Santoni et al., "Lamb Wave-Mode Tuning of Piezoelectric Wafer Active Sensors for Structural Health Monitoring", Transactions of the ASME, vol. 129, Dec. 2007, pp. 752-763.

Office Action, dated May 15, 2013, regarding USPTO U.S. Appl. No. 13/084,276, 15 pages.

* cited by examiner

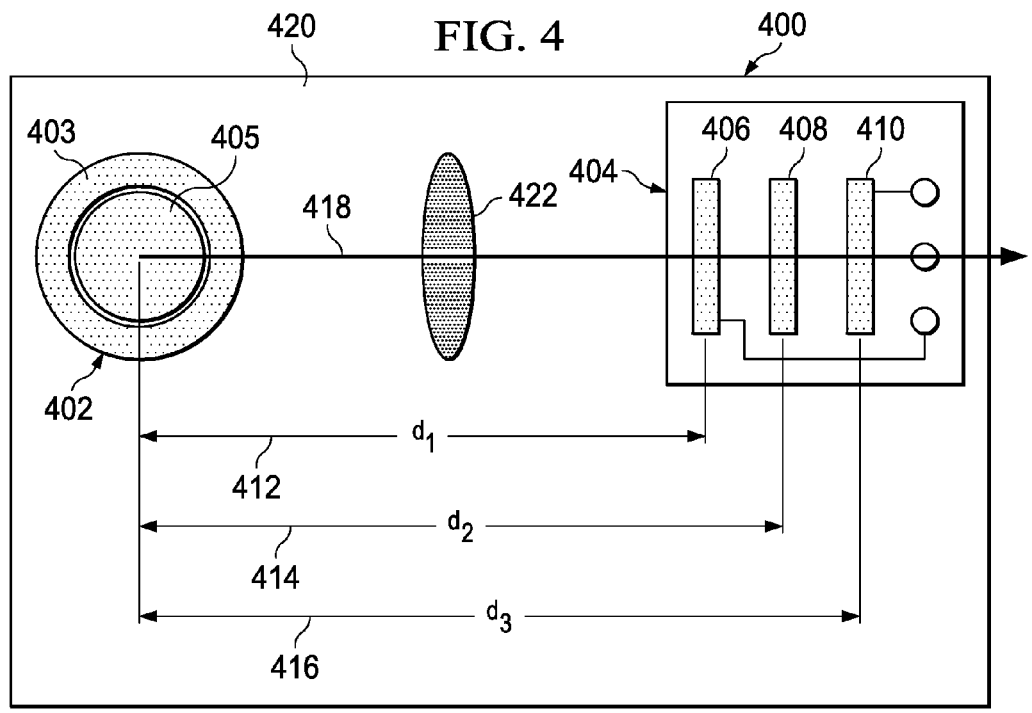
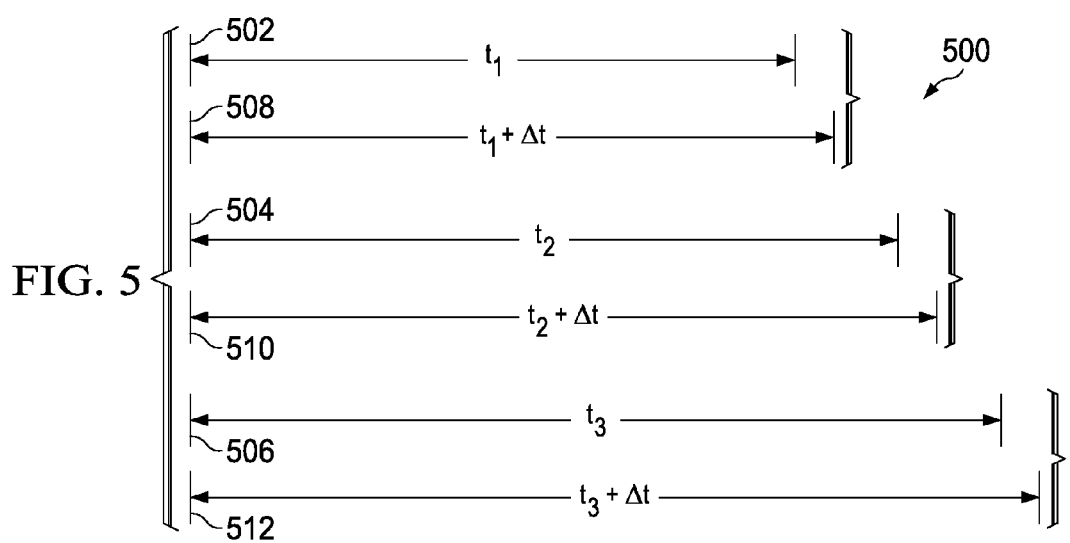

TRANSDUCER BASED HEALTH MONITORING SYSTEM

CROSS-REFERENCE TO RELATED APPLICATION

This application is related to the following patent application: entitled "Time Delay Based Health Monitoring System Using a Sensor Network", Ser. No. 13/084,276, filed even date hereof, assigned to the same assignee, and incorporated herein by reference.

BACKGROUND INFORMATION

1. Field

The present disclosure relates generally to monitoring aircraft structures and, in particular, to monitoring aircraft structures for inconsistencies. Still more particularly, the present disclosure relates to a method and apparatus for detecting inconsistencies in aircraft structures using signals sent through the aircraft structures.

2. Background

Composite and metallic aircraft structures may be susceptible to internal changes that may occur from fatigue, impacts, and/or other events or conditions. Composite materials typically have a minimal visual indication of these types of changes. As a result, an aircraft may be inspected to access the integrity of the structure on a periodic basis, or after visual indications of surface inconsistencies, such as a dent or a scratch.

For example, impacts to a structure, such as an aircraft, may occur during cargo loading and unloading. Inspections of the structure of an aircraft may be time-consuming and costly in terms of the time and skill needed to perform the inspection. Further, an airline may incur a loss of revenue from the aircraft being out of service.

Structural health monitoring techniques have been developed and used to monitor materials and structures. These techniques often build the health monitoring systems into the structures. These health monitoring systems may be used to determine whether changes have occurred to these materials and structures over time.

Sudden changes in environments, such as electromagnetic effects, mechanical stresses, and other environmental effects may affect various materials and structures over time. By having health monitoring systems built into or associated with the structures to monitor the structures during use, appropriate measures and responses may be taken to prevent inconsistencies and may prolong the life span of these structures.

The monitoring of structures may include various non-destructive elevation methods, such as ultrasonic testing or x-ray testing. Ultrasonic testing uses contact-based transducers to mechanically scan a structure. These transducers may be surface-mounted on the structure or may be embedded in the structure to generate and propagate signals into the structure being monitored.

A structural health monitoring system uses transducers to transmit waveforms at various frequency ranges and acquire data from the responses. Although structural health monitoring systems may provide an automated onboard system for detecting and characterizing inconsistencies or changes that may require maintenance, these types of systems may require updates and adjustments when maintenance, modifications, and reconfigurations of an aircraft occur.

For example, if a skin panel is changed, if a landing gear is modified, or other changes occur, additional transducers may need to be moved or configured for use with the replaced or new components. These and other types of updates to the structural health monitoring system are time consuming and expensive. The time needed to update the health monitoring system may make the aircraft unavailable for use longer than desired.

Therefore, it would be advantageous to have a method and apparatus that takes into account some of the issues discussed above, as well as possibly other issues.

SUMMARY

In one advantageous embodiment, a method for detecting an inconsistency in an object is provided. A signal sent from a first transducer unit is received at a second transducer unit. The signal is sent along a path through an object from the first transducer unit to the second transducer unit. The second transducer unit has segments. A velocity is identified at each segment in the segments for a number of modes for the signal to form identified velocities. A determination is made as to whether the inconsistency is present along the path through the object using the identified velocities for the number of modes for the signal.

In another advantageous embodiment, an apparatus comprises a signal analysis module. The signal analysis module is configured to identify velocities for a number of modes for a signal sent from a first transducer unit and received at segments for a second transducer unit. The signal is sent along a path through an object from the first transducer unit to the second transducer unit. The signal analysis module is configured to determine whether an inconsistency is present along the path through the object using the identified velocities for the number of modes for the signal.

In another advantageous embodiment, a health monitoring system of an aircraft comprises a transducer system and a signal analysis module. The transducer system is associated with a number of structures in the aircraft. The signal analysis module is configured to cause a first transducer unit in the transducer system to send a signal along a path in an object to a second transducer unit in the transducer system. The second transducer unit has segments. A velocity for each segment for a number of modes for the signal is identified to form identified velocities for the number of modes for the signal. The signal analysis module is configured to determine whether an inconsistency is present along the path through the object using the identified velocities for the number of modes for the signal.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

FIG. 4 is an illustration of a transducer system in accordance with an advantageous embodiment;

FIG. 5 is an illustration of times at which a signal transmitted by a first transducer unit reaches a second transducer unit in accordance with an advantageous embodiment;

DETAILED DESCRIPTION

Figure 1:
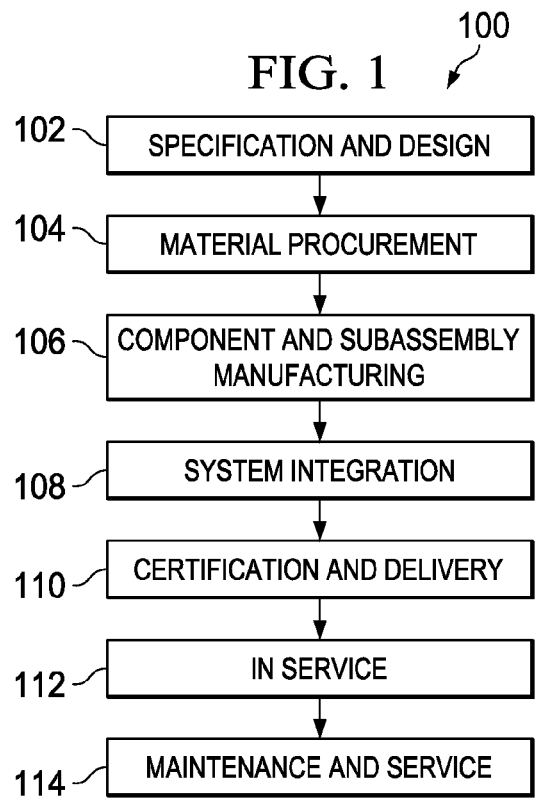
FIG. 1 is an illustration of an aircraft manufacturing and service method in accordance with an advantageous embodiment.
Figure 2:
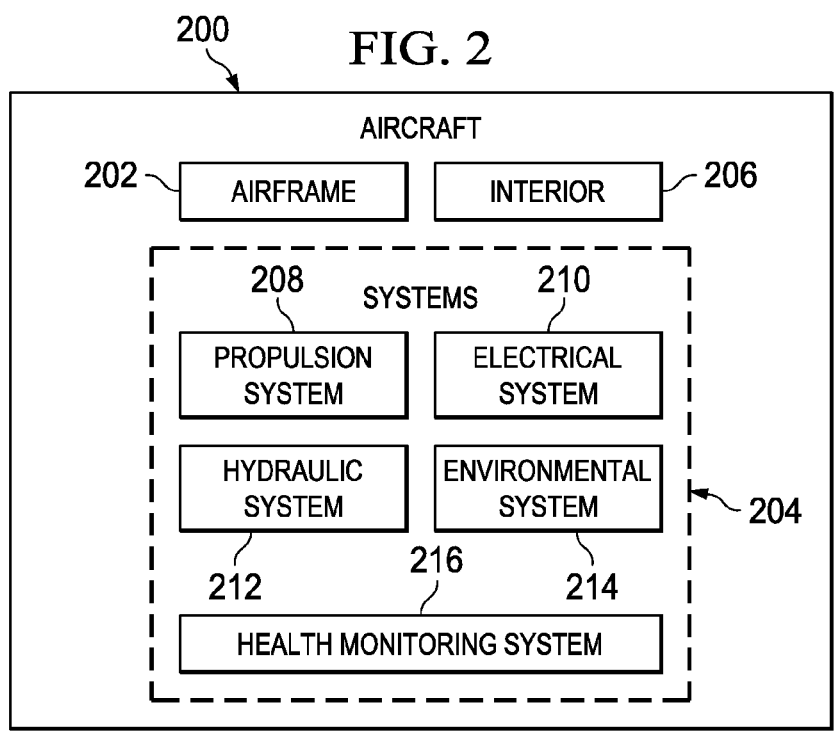
FIG. 2 is an illustration of an aircraft in which an advantageous embodiment may be implemented.

Referring more particularly to the drawings, advantageous embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems in plurality of systems 204 include one or more of propulsion system 208, electrical system 210, hydraulic system 212, environmental system 214, and health monitoring system 216. Any number of other systems may be included. Although an aerospace example is shown, different advantageous embodiments may be applied to other industries, such as the automotive industry.

Apparatuses and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example may also include item A, item B, and item C or item B and item C.

In one illustrative example, components or subassemblies produced in component and subassembly manufacturing 106 in FIG. 1 for health monitoring system 216 may be fabricated or manufactured in a manner similar to components or subassemblies produced for health monitoring system 216 while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments may substantially expedite the assembly of and/or reduce the cost of aircraft 200.

The different advantageous embodiments recognize and take into account a number of different considerations. For example, the different advantageous embodiments recognize and take into account that many currently used health monitoring systems that use baseline data may have a higher rate of false positive indications of inconsistencies than desired. These false indications may occur from different environmental and operational variations.

For example, the different advantageous embodiments recognize and take into account that many currently used health monitoring systems rely on baseline data. Baseline data is data generated from sending signals through structures in the aircraft during a time at which the structures are considered to have no inconsistencies.

The different advantageous embodiments recognize and take into account that this baseline data is typically generated under conditions that may vary from those present during operating conditions. For example, the data may be generated using the temperature, pressure, and other environmental factors that are present, while the aircraft or parts are on the ground or not installed. These parameters may change when the aircraft is operating. The parameters may also change between various phases of flight such as taxiing, takeoff, en route, landing, and other phases. Temperature, pressure, and other changes in the environment around an aircraft during operation of the aircraft may result in false indications of the presence of inconsistencies when compared to baseline data taken during generation of the baseline data when the aircraft is not in operation.

The different advantageous embodiments recognize and take into account that currently used health monitoring systems may attempt to compensate for changes in the environment. The different advantageous embodiments recognize and take into account that currently used systems may attempt to obtain data for the structures without inconsistencies under the different operating conditions that may occur to take into account changes that may occur in the environment. This information may then be used as a comparison to data generated during the operation of the aircraft to determine whether inconsistencies are present.

The different advantageous embodiments recognize and take into account, however, that this type of compensation for operating conditions may require recording more data than desired. The amount of data obtained for different environmental conditions may use more storage space than desirable in a health monitoring system. Further, the different advantageous embodiments also recognize and take into account that it may not be possible to record data from all possible types of operating conditions that may be encountered during the operation of the aircraft.

The different advantageous embodiments also recognize and take into account that this type of health monitoring system may also require re-recording of data when sensors are replaced. The different advantageous embodiments recognize and take into account that it would be desirable to detect inconsistencies without requiring the use of baseline data.

Thus, the different advantageous embodiments provide a method and apparatus for detecting an inconsistency in an object. A signal sent from a first transducer unit is received at a second transducer unit. The signal is sent on a path through an object from the first transducer unit to the second transducer unit. The second transducer unit has segments. A velocity is identified at each segment in the segments for a number of modes for the signal to form identified velocities. A determination is made as to whether the inconsistency is present along the path through the object using the identified velocities for the number of modes for the signal.

Figure 3:
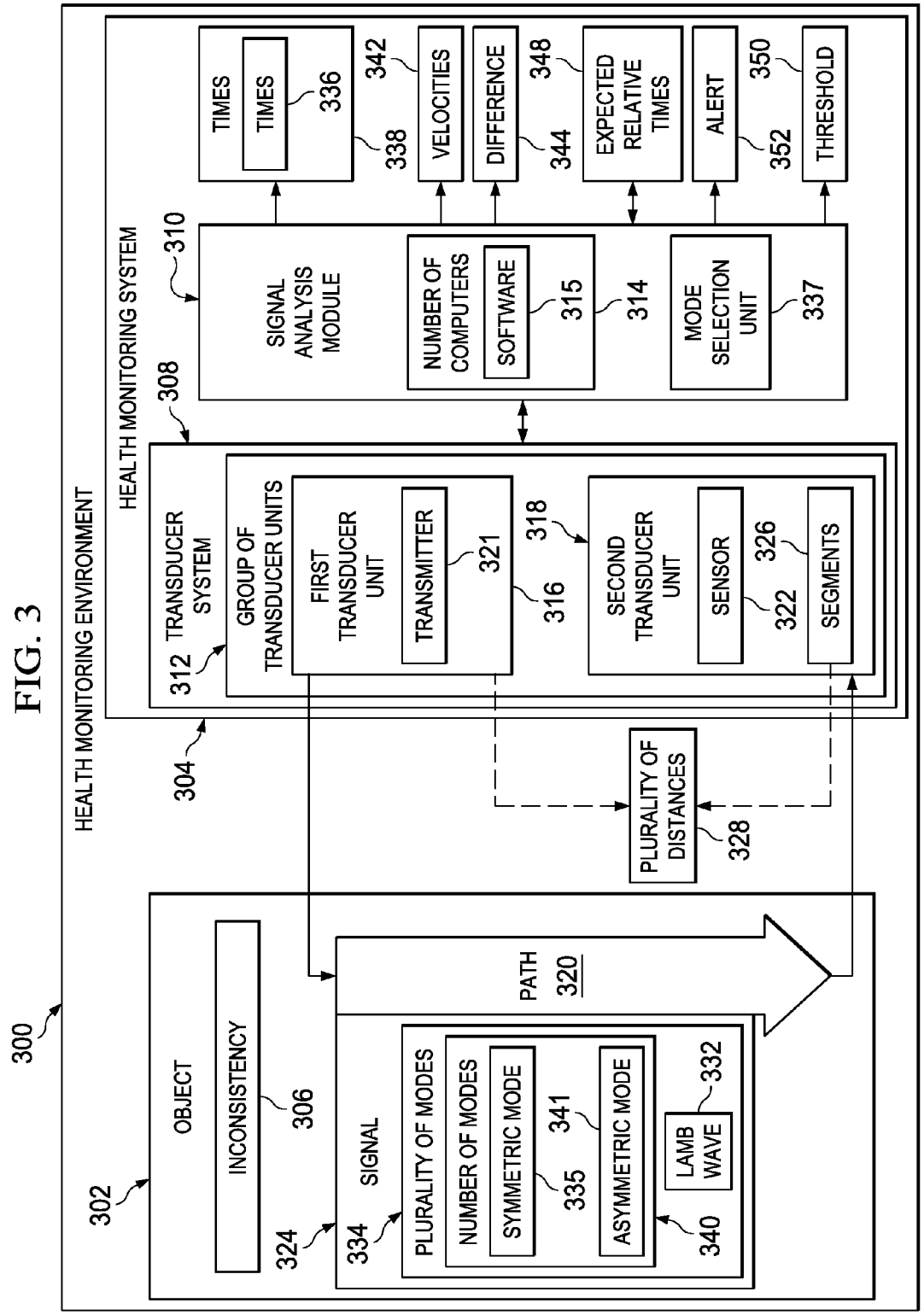
FIG. 3 is an illustration of a health monitoring environment in accordance with an advantageous embodiment.

With reference now to FIG. 3, an illustration of a health monitoring environment is depicted in accordance with an advantageous embodiment. Health monitoring environment 300 is an example of an environment that may be implemented in aircraft 200 in FIG. 2. As depicted, health monitoring environment 300 includes object 302 and health monitoring system 304 in this illustrative example.

In this illustrative example, object 302 is an example of an object that may be monitored using health monitoring system 304. In this illustrative example, object 302 may take various forms. In this example, object 302 takes the form of aircraft 200 or a structure or system within aircraft 200 in FIG. 2.

Health monitoring system 304 is associated with object 302. A first component may be considered to be associated with a second component by being secured to the second component, bonded to the second component, fastened to the second component, and/or connected to the second component in some other suitable manner. The first component may also be connected to the second component using a third component. The first component may also be considered to be associated with the second component by being formed as part of and/or an extension of the second component.

In these depicted examples, health monitoring system 304 is configured to detect a presence of inconsistency 306 in object 302. Inconsistency 306 may be any element or portion of object 302 that does not have a desired or expected state. Inconsistency 306 may be, for example, at least one of a delamination, a number of voids, and/or some other suitable type of inconsistency.

As depicted, health monitoring system 304 comprises transducer system 308 and signal analysis module 310. Transducer system 308 comprises group of transducer units 312. A transducer unit within group of transducer units 312 may function as a transmitter, a sensor, or both, depending on the particular implementation.

Transducers within group of transducer units 312 may be implemented using any known transducer configured to generate signals that may be sent through object 302. Additionally, transducers within group of transducer units 312 may also include transducers configured to receive signal 324 sent through object 302.

In these illustrative examples, group of transducer units 312 includes first transducer unit 316 and second transducer unit 318. First transducer unit 316 may be configured to function as transmitter 321. Second transducer unit 318 may be configured to function as sensor 322.

Further, in these depicted examples, second transducer unit 318 has segments 326. Segments 326 may be transducers in second transducer unit 318 in these examples. In other examples, segments 326 may be in a transducer in second transducer unit 318.

First transducer unit 316 has plurality of distances 328 from first transducer unit 316 to segments 326 in second transducer unit 318. In other words, each distance in plurality of distances 328 is from first transducer unit 316 to a particular segment in segments 326.

In these illustrative examples, transducer system 308 is connected to signal analysis module 310. Signal analysis module 310 is configured to control transducer system 308 in monitoring or testing of object 302 for inconsistency 306.

In these illustrative examples, signal analysis module 310 is comprised of hardware, software, or a combination of the two. For example, signal analysis module 310 may be comprised of number of computers 314 with software 315.

Signal analysis module 310 is configured to cause first transducer unit 316 to send signal 324 along path 320 through object 302 from first transducer unit 316 to second transducer unit 318. Path 320 may also be referred to as a wave propagation path.

In this illustrative example, signal 324 takes the form of Lamb wave 332. A Lamb wave is a wave that propagates in solid media. For example, a Lamb wave may propagate within the thickness of an object, such as a plate or other type of object.

Further, signal 324 has plurality of modes 334. A mode, as used herein, is a component of a waveform that makes up a signal. A mode is one type of physical propagation of waveforms in these illustrative examples. Plurality of modes 334 includes symmetric mode 335 and asymmetric mode 341. Asymmetric mode 341 may be affected more by certain types of inconsistencies in object 302 as compared to symmetric mode 335. In particular, asymmetric mode 341 may be affected more by inconsistencies in the form of delaminations as compared to symmetric mode 335.

As one illustrative example, object 302 may be a composite object comprising composite materials. With delamination of composite materials, asymmetric mode 341 is affected more than symmetric mode 335. Of course, for other types of materials for other types of object 302, other modes may be more affected by inconsistencies. For example, object 302 may comprise a material selected from at least one of a metal, titanium, aluminum, steel, and some other suitable material. Path 320 for signal 324 passes through the material in object 302.

In these depicted examples, segments 326 for second transducer unit 318 are substantially aligned with path 320 for signal 324. As signal 324 travels along path 320 to second transducer unit 318, signal 324 reaches segments 326 at times 338. Times 338 are identified by signal analysis module 310. In these examples, times 338 may be referred to as times of flight or times of travel for signal 324.

In these illustrative examples, different modes within plurality of modes 334 for signal 324 may arrive at different segments in segments 326 for second transducer unit 318 at different times within times 338.

In these illustrative examples, signal analysis module 310 identifies times 336 within times 338 for number of modes 340 for signal 324. Times 336 are the times at which number of modes 340 for signal 324 reaches segments 326 for second transducer unit 318.

As depicted, signal analysis module 310 includes mode selection unit 337. Mode selection unit 337 identifies number of modes 340 in plurality of modes 334 for which times 336 are identified. Number of modes 340 is selected for use in determining whether inconsistency 306 is present. Number of modes 340 is selected as ones that may provide a greatest desired ability to identify inconsistency 306 in object 302.

In these illustrative examples, one mode is selected for number of modes 340. In particular, number of modes 340 takes the form of asymmetric mode 341 in these examples. In other illustrative examples, additional modes may also be identified.

Signal analysis module 310 identifies times 336 for asymmetric mode 341 for signal 324 at which signal 324 is detected by segments 326 for second transducer unit 318. In some illustrative examples, signal analysis module 310 identifies velocities 342 for asymmetric mode 341 for signal 324 at each of segments 326. In other words, signal analysis module 310 identifies velocities 342 for asymmetric mode 341 for signal 324 when signal 324 reaches segments 326.

In some illustrative examples, signal analysis module 310 identifies times 336 and velocities 342. In other examples, signal analysis module 310 uses times 336 and plurality of distances 328 to identify velocities 342. In still other examples, signal analysis module 310 uses plurality of distances 328 and velocities 342 to identify times 336.

When inconsistency 306 is not present along path 320 in object 302, velocities 342 for signal 324 at each of segments 326 may be substantially equal. However, when inconsistency 306 is present along path 320 in object 302, velocities 342 may be different.

For example, when signal 324 is detected at segments 326 for second transducer unit 318, signal analysis module 310 identifies the velocity for a mode in number of modes 340 for signal 324 at the time of detection at each of segments 326. Further, signal analysis module 310 is configured to determine whether difference 344 between velocities 342 is greater than threshold 350. Difference 344 may be greater than threshold 350 when inconsistency 306 is present along path 320 for signal 324.

Signal analysis module 310 generates alert 352 if difference 344 between velocities 342 is greater than threshold 350. Alert 352 is an indication that inconsistency 306 is present in object 302. In these illustrative examples, alert 352 may be a signal, a message, or some other suitable type of alert. Alert 352 may include other information. For example, alert 352 may include the particular path, the transmitting and receiving transducer, the time at which the inconsistency was detected, operating conditions, state of the aircraft, and other suitable information.

In some illustrative examples, inconsistency 306 may be identified without using velocities 342. For example, when inconsistency 306 is not present, signal 324 may be detected by segments 326 at expected relative times 348 based on known values for plurality of distances 328 and the assumption that signal 324 may reach each of segments 326 at substantially the same velocity when inconsistency 306 is not present.

A difference between times 336 identified for number of modes 340 for signal 324 and expected relative times 348 greater than a selected threshold indicates the presence of inconsistency 306 along path 320.

In still other illustrative examples, signal analysis module 310 may compare the inverses of velocities 342 to identify whether inconsistency 306 is present along path 320.

Thus, the different advantageous embodiments in health monitoring environment 300 identify a presence of inconsistency 306 without needing or using baseline data.

The illustration of health monitoring environment 300 in FIG. 3 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, although object 302 has been described with respect to an aircraft, object 302 may take other forms. For example, object 302 may be selected from one of a mobile platform, a stationary platform, a land-based structure, an aquatic-based structure, a space-based structure, an aircraft, an airplane, a helicopter, a surface ship, a tank, a personnel carrier, a train, a spacecraft, a space station, a satellite, a submarine, an automobile, a power plant, a bridge, a dam, a manufacturing facility, a building, a composite structure for the aircraft, a skin panel, an engine, a fuselage, a wing, a rib, and a stringer.

With reference now to FIG. 4, an illustration of a transducer system is depicted in accordance with an advantageous embodiment. In this illustrative example, transducer system 400 is an example of one implementation for transducer system 308 in FIG. 3.

As depicted, transducer system 400 includes first transducer unit 402 and second transducer unit 404. First transducer unit 402 functions as a transmitter. Second transducer unit 404 functions as a sensor.

In this illustrative example, first transducer unit 402 has segment 403 and segment 405. Second transducer unit 404 has segments 406, 408, and 410. All of these segments are transducers in this depicted example.

As illustrated, distance 412, $d_1$, is the distance between the center of first transducer unit 402 and segment 406. Distance 414, $d_2$, is the distance between the center of first transducer unit 402 and segment 408. Distance 416, $d_3$, is the distance between the center of first transducer unit 402 and segment 410.

First transducer unit 402 is configured to transmit a signal along path 418 through object 420. Segments 406, 408, and 410 are substantially aligned with path 418 in this example. A signal transmitted from first transducer unit 402 and traveling along path 418 reaches the segments for second transducer unit 404 in the order of segment 406, segment 408, and segment 410.

When an inconsistency is not present along path 418 in object 420, the signal is detected at segments 406, 408, and 410 having substantially the same velocity. However, when an inconsistency is present along path 418 in object 420, the velocities for the signal detected at the different segments may be different.

For example, when inconsistency 422 is present in object 420, the time it takes for a signal transmitted by first transducer unit 402 to reach each of segments 406, 408, and 410 of second transducer unit 404 may be delayed as compared to the time it takes for the signal to reach the segments when inconsistency 422 is not present. This delay may be substantially equal for the time it takes to reach segment 406, the time it takes to reach segment 408, and the time it takes to reach segment 410.

With reference now to FIG. 5, an illustration of times at which a signal transmitted by a first transducer unit reaches a second transducer unit is depicted in accordance with an advantageous embodiment. In particular, times 500 are the times at which a signal transmitted by first transducer unit 402 reaches a segment of second transducer unit 404 when inconsistency 422 is present and when inconsistency 422 is not present in object 420 in FIG. 4. These times may also be referred to as times of flight.

In this illustrative example, time 502, $t_1$, is the time it takes for the signal to reach segment 406 of second transducer unit 404 when inconsistency 422 is not present. Time 504, $t_2$, is the time it takes for the signal to reach segment 408 of second transducer unit 404 when inconsistency 422 is not present. Further, time 506, $t_3$, is the time it takes for the signal to reach segment 410 of second transducer unit 404 when inconsistency 422 is not present.

In other words, when inconsistency 422 is not present, the velocities of the signal detected at segments 406, 408, and 410 are substantially equal as indicated by the following:

$$\frac{d_1}{t_1} = \frac{d_2}{t_2} = \frac{d_3}{t_3}, V_1 = V_2 = V_3.$$

where $V_1$ is the velocity of the signal detected at segment 406, $V_2$ is the velocity of the signal detected at segment 408, and $V_3$ is the velocity of the signal detected at segment 410.

When inconsistency 422 is present, times 502, 504, and 506 may be delayed by substantially the same time delay, $\Delta t$. As depicted, when inconsistency 422 is present, the signal takes time 508 to reach segment 406, time 510 to reach segment 408, and time 512 to reach segment 410. Time 508, time 510, and time 512 are longer time periods than time 502, time 504, and time 506, respectively, by substantially the same amount, $\Delta t$.

In this manner, when inconsistency 422 is present, the velocities of the signal detected at segments 406, 408, and 410 are different as indicated by the following:

$$\frac{d_1}{\Delta t + t_1} \neq \frac{d_2}{\Delta t + t_2} \neq \frac{d_3}{\Delta t + t_3}, V_1 \neq V_2 \neq V_3.$$

Identification of inconsistencies may be performed by comparing velocities. These velocities are identified from signals detected by transducers in which the signals are sent at substantially the same time through an object. The identification of the inconsistencies does not use prior baseline data. This process may be performed to identify inconsistencies even under changing operational and environmental conditions of the object.

Figure 6:
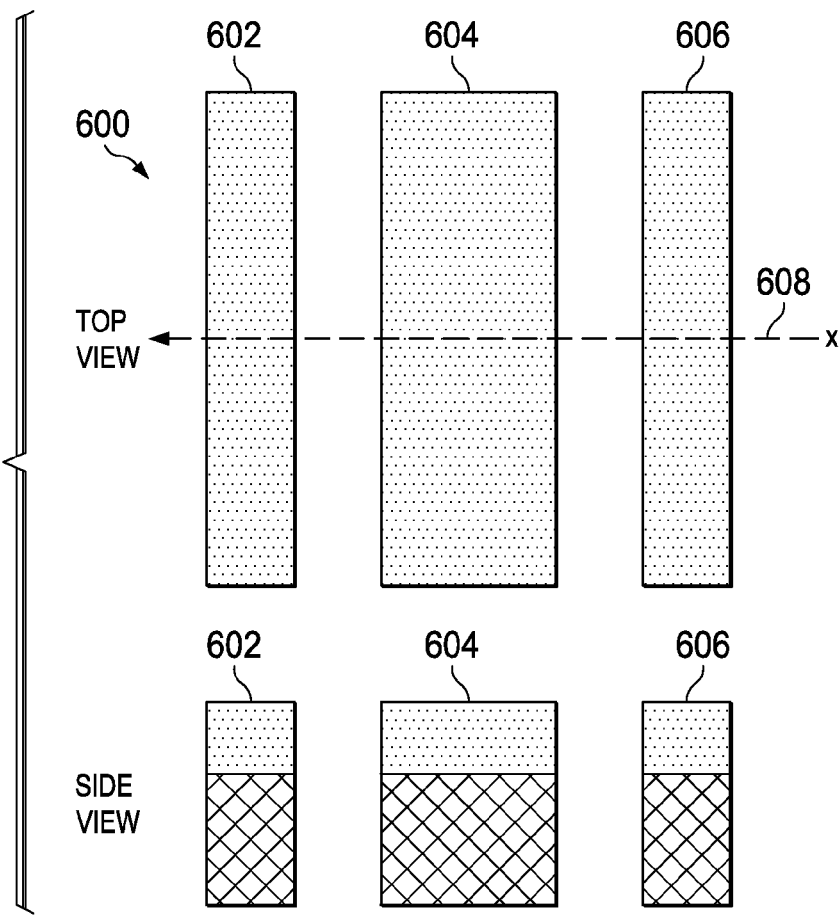
FIG. 6 is an illustration of a three-segment transducer unit in accordance with an advantageous embodiment.

With reference now to FIGS. 6-9, examples of transducer units are depicted in accordance with an advantageous embodiment. In FIG. 6, an illustration of a three-segment transducer unit is depicted in accordance with an advantageous embodiment. In this illustrative example, transducer unit 600 is shown in a top view and a side view. Transducer unit 600 is an example of one implementation for second transducer unit 318 in FIG. 3.

As depicted, transducer unit 600 comprises transducers 602, 604, and 606. These three transducers are examples of segments 326 in FIG. 3. As can be seen, transducer unit 600 is symmetric along axis 608.

Figure 7:
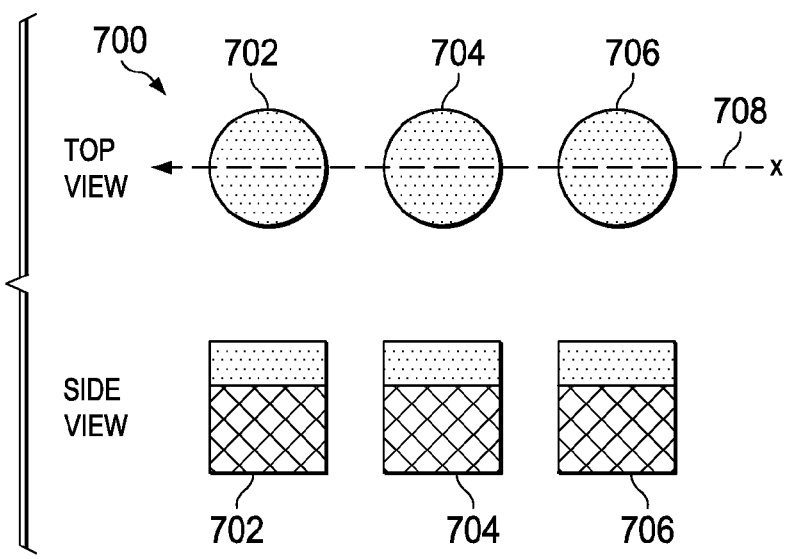
FIG. 7 is another illustration of a three-segment transducer unit in accordance with an advantageous embodiment.

In FIG. 7, another illustration of a three-segment transducer unit is depicted in accordance with an advantageous embodiment. In this illustrative example, transducer unit 700 comprises transducer 702, transducer 704, and transducer 706. Transducer unit 700 is symmetric about axis 708.

Figure 8:
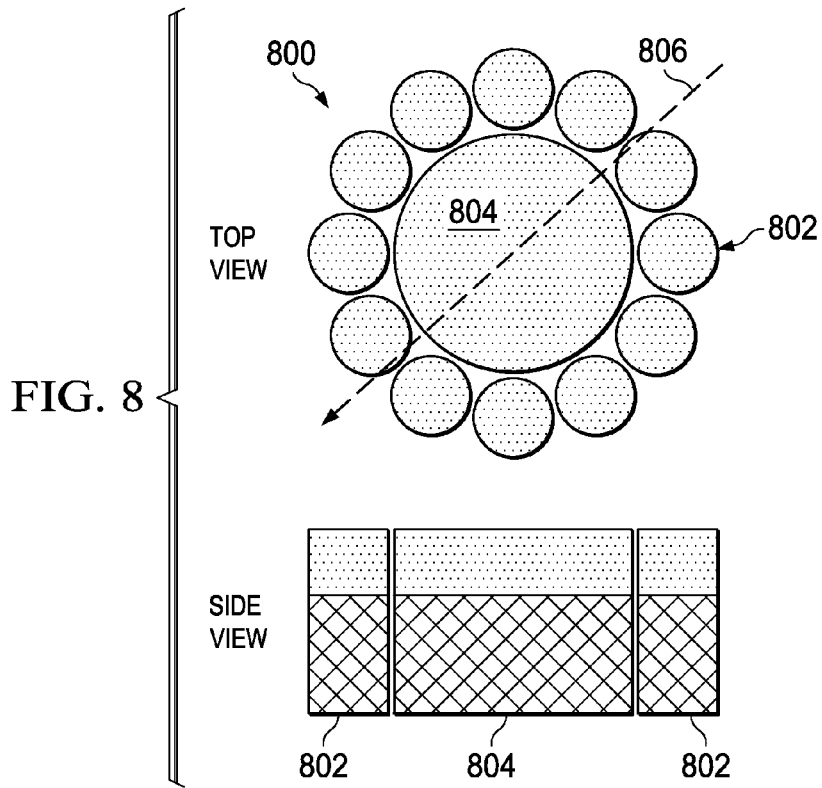
FIG. 8 is an illustration of a ring-based transducer unit in accordance with an advantageous embodiment.

With reference now to FIG. 8, an illustration of a ring-based transducer unit is depicted in accordance with an advantageous embodiment. In this illustrative example, transducer unit 800 comprises plurality of transducers 802 and transducer 804. Plurality of transducers 802 are arranged in the form of a ring around transducer 804 in this illustrative example. Transducer unit 800 is symmetric about axis 806 in these examples.

Figure 9:
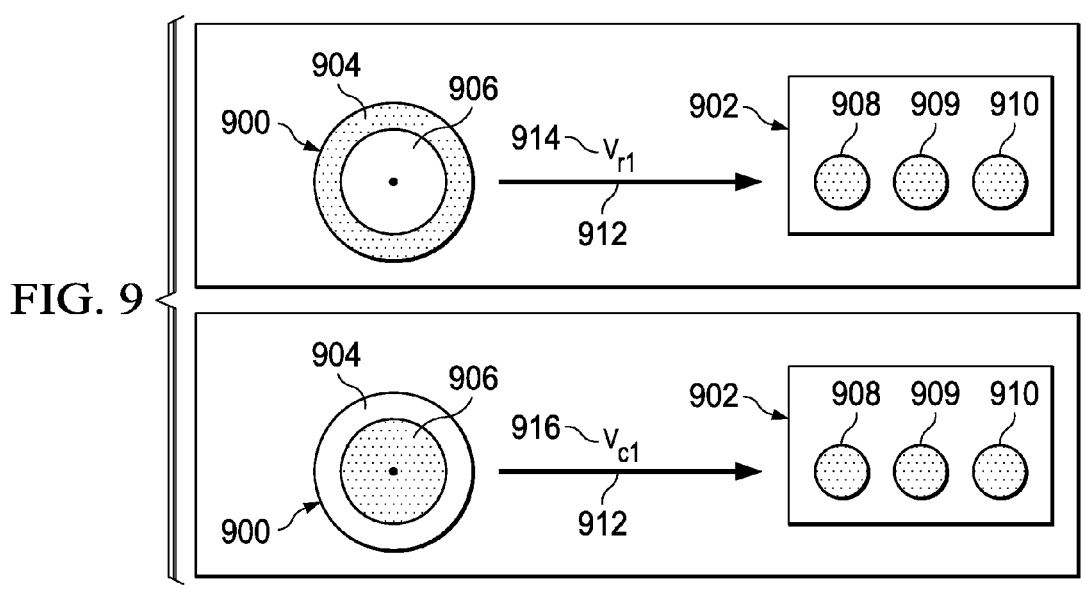
FIG. 9 is an illustration of signals detected by two different segments of a transducer unit in accordance with an advantageous embodiment.

With reference now to FIG. 9, an illustration of signals detected by two different segments of a transducer unit is depicted in accordance with an advantageous embodiment. In this illustrative example, transducer unit 900 functions as a transmitter, while transducer unit 902 functions as a sensor. Transducer unit 900 has ring segment 904 and circular segment 906. Transducer unit 902 has circular segment 908, circular segment 909, and circular segment 910.

As depicted in this illustrative example, path 912 is formed between transducer unit 900 and transducer unit 902. Activation of different segments for the transducer units allows six different Lamb wave signals to be obtained.

For example, when ring segment 904 of transducer unit 900 is activated, signal 914, $V_{r1}$, is detected by circular segment 908 of transducer unit 902. Further, when circular segment 906 is activated, signal 916, $V_{c1}$, is detected by circular segment 908 of transducer unit 902.

Further, two different Lamb wave signals (not shown), $V_{c2}$ and $V_{c3}$, may be detected by circular segment 909 and circular segment 910 of transducer unit 902 when circular segment 906 of transducer unit 900 is activated. In a similar fashion, two different Lamb wave signals (not shown), $V_{r2}$ and $V_{r3}$, may be detected by circular segment 909 and circular segment 910 of transducer unit 902 when ring segment 904 of transducer unit 900 is activated.

In this illustrative example, the modes for signal 914 and signal 916 may have substantially identical arrival times at circular segment 908, respectively, but different amplitudes. Further, the amplitudes of the symmetric ($S_0$) modes and the asymmetric ($A_0$) modes change at different rates as the size of the segment in the transmitting transducer unit that transmits the signal varies.

In other words, the amplitudes of the symmetric modes and the asymmetric modes change depending on which segment is activated to transmit in transducer unit 900. Additionally, the rate at which the amplitude of each mode in the modes for the signal changes, with respect to the size of the particular segment transmitting in transducer unit 900, is not based on the distance between transducer unit 900 and transducer unit 902.

Signal 914 and signal 916 may be used by, for example, signal analysis module 310 in FIG. 3, to identify a number of modes for use in identifying inconsistencies in an object. For example, signal 914 and signal 916 may be excited at ring segment 904 and circular segment 906 for transducer unit 900. The amplitudes of the symmetric modes in signal 914 and signal 916 are normalized such that the amplitudes of the symmetric modes are substantially equal.

The symmetric modes may then be removed by subtracting signal 914, $V_{r1}$, from signal 916, $V_{c1}$. In other words, the symmetric modes are subtracted from each other such that only the asymmetric mode remains. The signal formed by the subtraction does not preserve the amplitude information. This signal does, however, retain arrival time information for the asymmetric mode. In this manner, time information may be identified using the asymmetric mode.

In particular, the asymmetric mode signal or waveform formed contains information for the time of travel between transducer unit 900 and transducer unit 902. In this manner, time information may be identified using the asymmetric mode waveform.

Figure 10:
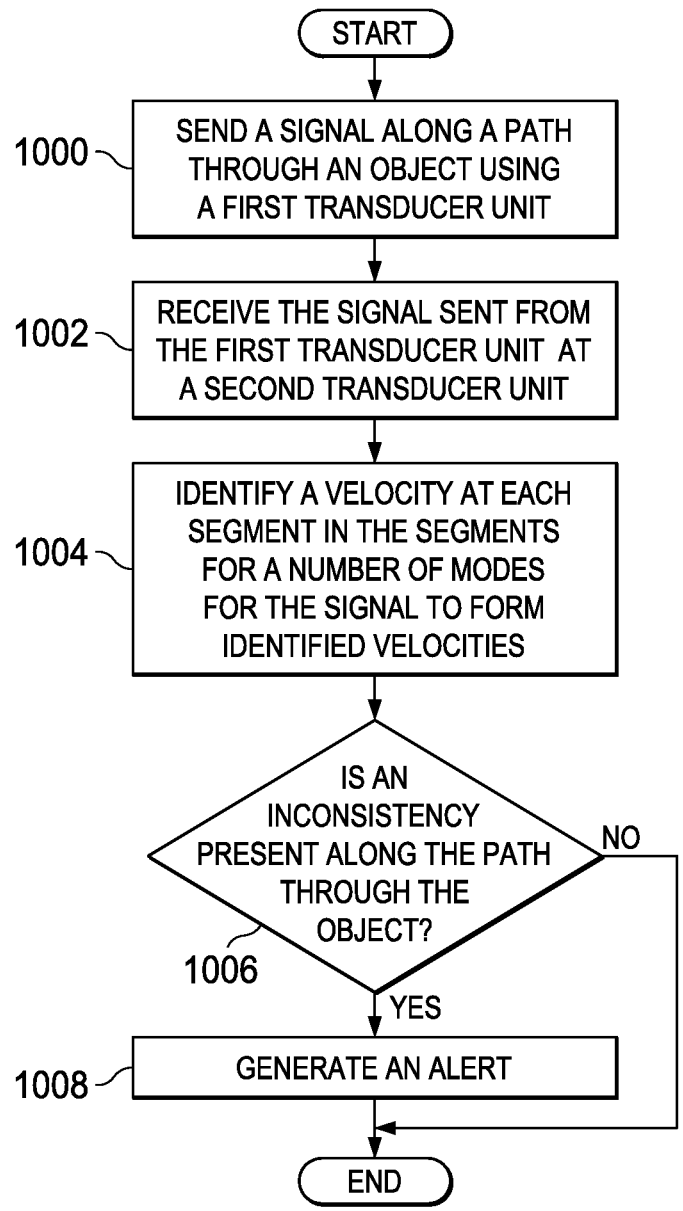
FIG. 10 is an illustration of a flowchart of a process for detecting an inconsistency in an object in accordance with an advantageous embodiment.

With reference now to FIG. 10, an illustration of a flowchart of a process for detecting an inconsistency in an object is depicted in accordance with an advantageous embodiment. The process illustrated in FIG. 10 may be implemented in health monitoring environment 300 in FIG. 3. In particular, this process may be implemented within signal analysis module 310 in FIG. 3.

The process begins by sending a signal along a path through an object using a first transducer unit (operation 1000). This first transducer unit functions as a transmitter. The signal sent from the first transducer unit is received at a second transducer unit (operation 1002). The second transducer unit functions as a sensor. The second transducer unit has segments.

The process then identifies a velocity at each segment in the segments for a number of modes for the signal to form identified velocities (operation 1004). In this illustrative example, the number of modes includes one type of mode. In particular, the mode is an asymmetric mode.

A determination is made as to whether an inconsistency is present along the path through the object (operation 1006) using the identified velocities for the number of modes for the signal. In operation 1006, the determination is made by determining whether a difference between the identified velocities is greater than a threshold. An inconsistency is present along the path when the difference is greater than the threshold.

If an inconsistency is not present, the process terminates. Otherwise, if an inconsistency is present, the process generates an alert (operation 1008), with the process terminating thereafter.

The flowcharts and block diagrams in the different depicted embodiments illustrate the architecture, functionality, and operation of some possible implementations of apparatuses and methods in different advantageous embodiments. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

Figure 11:
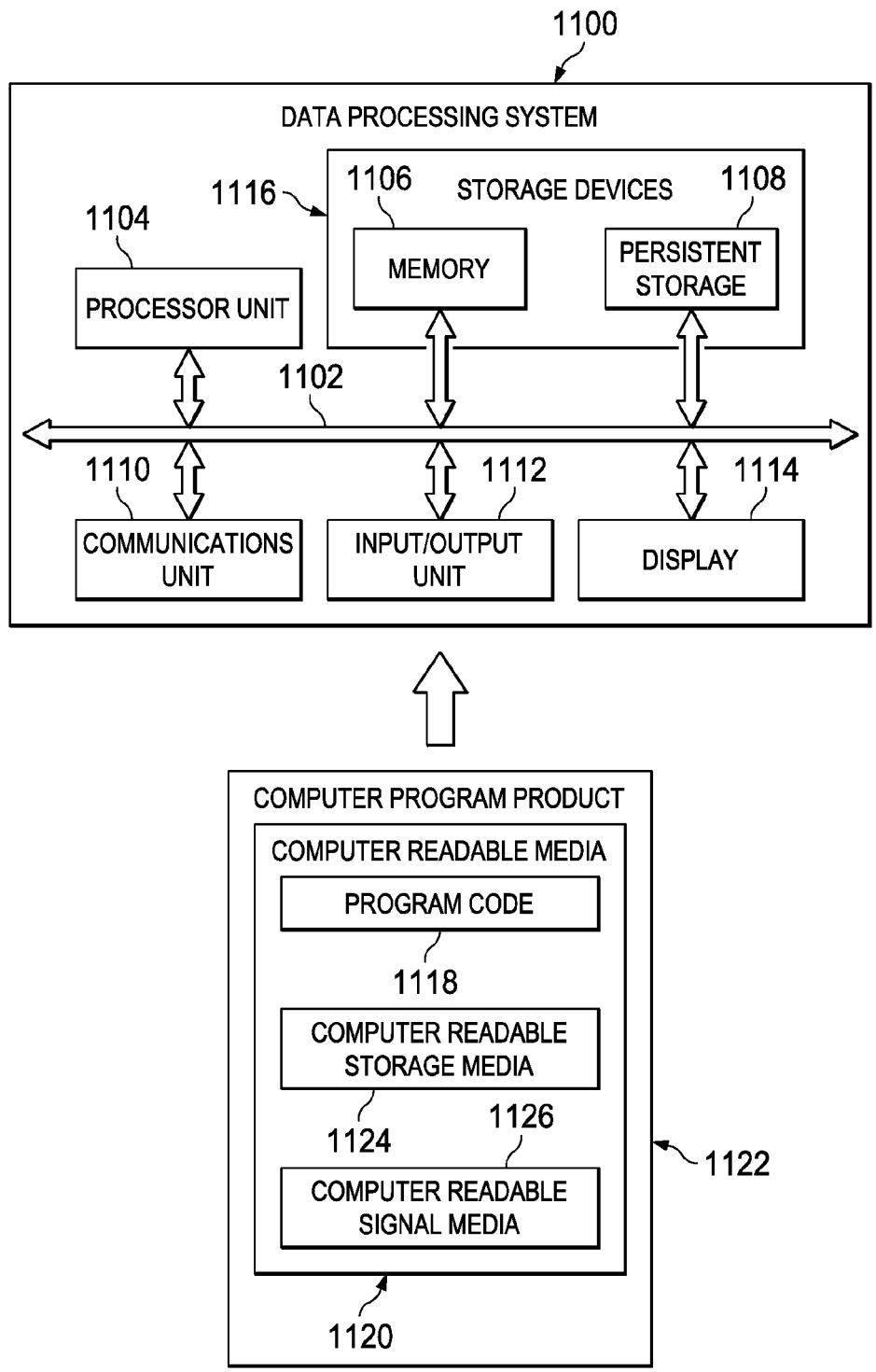
FIG. 11 is an illustration of a data processing system in accordance with an advantageous embodiment.

Turning now to FIG. 11, an illustration of a data processing system is depicted in accordance with an advantageous embodiment. In this illustrative example, data processing system 1100 includes communications fabric 1102, which provides communications between processor unit 1104, memory 1106, persistent storage 1108, communications unit 1110, input/output (I/O) unit 1112, and display 1114.

Processor unit 1104 serves to execute instructions for software that may be loaded into memory 1106. Processor unit 1104 may be a number of processors, a multi-processor core, or some other type of processor, depending on the particular implementation. A number, as used herein with reference to an item, means one or more items. Further, processor unit 1104 may be implemented using a number of heterogeneous processor systems in which a main processor is present with secondary processors on a single chip. As another illustrative example, processor unit 1104 may be a symmetric multi-processor system containing multiple processors of the same type.

Memory 1106 and persistent storage 1108 are examples of storage devices 1116. A storage device is any piece of hardware that is capable of storing information, such as, for example, without limitation, data, program code in functional form, and/or other suitable information either on a temporary basis and/or a permanent basis. Storage devices 1116 may also be referred to as computer readable storage devices in these examples. Memory 1106, in these examples, may be, for example, a random access memory or any other suitable volatile or non-volatile storage device. Persistent storage 1108 may take various forms, depending on the particular implementation.

For example, persistent storage 1108 may contain one or more components or devices. For example, persistent storage 1108 may be a hard drive, a flash memory, a rewritable optical disk, a rewritable magnetic tape, or some combination of the above. The media used by persistent storage 1108 may also be removable. For example, a removable hard drive may be used for persistent storage 1108.

Communications unit 1110, in these examples, provides for communications with other data processing systems or devices. In these examples, communications unit 1110 is a network interface card. Communications unit 1110 may provide communications through the use of either or both physical and wireless communications links.

Input/output unit 1112 allows for input and output of data with other devices that may be connected to data processing system 1100. For example, input/output unit 1112 may provide a connection for user input through a keyboard, a mouse, and/or some other suitable input device. Further, input/output unit 1112 may send output to a printer. Display 1114 provides a mechanism to display information to a user.

Instructions for the operating system, applications, and/or programs may be located in storage devices 1116, which are in communication with processor unit 1104 through communications fabric 1102. In these illustrative examples, the instructions are in a functional form on persistent storage 1108. These instructions may be loaded into memory 1106 for execution by processor unit 1104. The processes of the different advantageous embodiments may be performed by processor unit 1104 using computer implemented instructions, which may be located in a memory, such as memory 1106.

These instructions are referred to as program code, computer usable program code, or computer readable program code that may be read and executed by a processor in processor unit 1104. The program code in the different embodiments may be embodied on different physical or computer readable storage media, such as memory 1106 or persistent storage 1108.

Program code 1118 is located in a functional form on computer readable media 1120 that is selectively removable and may be loaded onto or transferred to data processing system 1100 for execution by processor unit 1104. Program code 1118 and computer readable media 1120 form computer program product 1122 in these examples. In one example, computer readable media 1120 may be computer readable storage media 1124 or computer readable signal media 1126. Computer readable storage media 1124 may include, for example, an optical or magnetic disk that is inserted or placed into a drive or other device that is part of persistent storage 1108 for transfer onto a storage device, such as a hard drive, that is part of persistent storage 1108.

Computer readable storage media 1124 may also take the form of a persistent storage, such as a hard drive, a thumb drive, or a flash memory, that is connected to data processing system 1100. In some instances, computer readable storage media 1124 may not be removable from data processing system 1100. In these examples, computer readable storage media 1124 is a physical or tangible storage device used to store program code 1118 rather than a medium that propagates or transmits program code 1118. Computer readable storage media 1124 is also referred to as a computer readable tangible storage device or a computer readable physical storage device. In other words, computer readable storage media 1124 is a media that can be touched by a person.

Alternatively, program code 1118 may be transferred to data processing system 1100 using computer readable signal media 1126. Computer readable signal media 1126 may be, for example, a propagated data signal containing program code 1118. For example, computer readable signal media 1126 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 1118 may be downloaded over a network to persistent storage 1108 from another device or data processing system through computer readable signal media 1126 for use within data processing system 1100. For instance, program code stored in a computer readable storage medium in a server data processing system may be downloaded over a network from the server to data processing system 1100. The data processing system providing program code 1118 may be a server computer, a client computer, or some other device capable of storing and transmitting program code 1118.

The different components illustrated for data processing system 1100 are not meant to provide architectural limitations to the manner in which different embodiments may be implemented. The different advantageous embodiments may be implemented in a data processing system including components in addition to or in place of those illustrated for data processing system 1100. Other components shown in FIG. 11 can be varied from the illustrative examples shown. The different advantageous embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 1104 may take the form of a hardware unit that has circuits that are manufactured or configured for a particular use. This type of hardware may perform operations without needing program code to be loaded into a memory from a storage device to be configured to perform the operations.

For example, when processor unit 1104 takes the form of a hardware unit, processor unit 1104 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 1118 may be omitted because the processes for the different embodiments are implemented in a hardware unit.

In still another illustrative example, processor unit 1104 may be implemented using a combination of processors found in computers and hardware units. Processor unit 1104 may have a number of hardware units and a number of processors that are configured to run program code 1118. With this depicted example, some of the processes may be implemented in the number of hardware units, while other processes may be implemented in the number of processors.

In another example, a bus system may be used to implement communications fabric 1102 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of one or more devices that are configured to transmit data, receive data, or transmit and receive data. A communications unit may be, for example, a modem or a network adapter, two network adapters, or some combination thereof. Further, a memory may be, for example, memory 1106, or a cache, such as found in an interface and memory controller hub that may be present in communications fabric 1102.

Thus, the different advantageous embodiments provide a method and apparatus for detecting an inconsistency in an object. A signal sent from a first transducer unit is received at a second transducer unit. The signal is sent on a path through an object from the first transducer unit to the second transducer unit. The second transducer unit has segments. A velocity is identified at each segment in the segments for a number of modes for the signal to form identified velocities. A determination is made as to whether the inconsistency is present along the path through the object using the identified velocities for the number of modes for the signal.

In one or more of the advantageous embodiments, inconsistencies are detected without any comparison with previously obtained baseline data. This type of identification of inconsistencies may be performed even in the presence of environmental variations, such as, for example, without limitation, temperature, pressure, and/or other environmental changes. In some advantageous embodiments, velocities are identified from signals sent through an object during a current state for a structure. These velocities are used to determine whether an inconsistency is present in the object. Baseline or other comparisons formed at prior times based on different environmental conditions are not used. As a result, the identification of an inconsistency is not affected by environmental conditions.

The description of the different advantageous embodiments has been presented for purposes of illustration and description, and is not intended to be exhaustive or limited to the advantageous embodiments in the form disclosed. Many modifications and variations will be apparent to those of ordinary skill in the art.

Further, different advantageous embodiments may provide different advantages as compared to other advantageous embodiments. The advantageous embodiment or embodiments selected are chosen and described in order to best explain the principles of the advantageous embodiments, the practical application, and to enable others of ordinary skill in the art to understand the disclosure for various advantageous embodiments with various modifications as are suited to the particular use contemplated.

What is claimed is:

1. A method for detecting an inconsistency in an object, the method comprising:
   receiving a signal sent from a first transducer unit at a second transducer unit, wherein the signal is sent along a path through an object from the first transducer unit to the second transducer unit and wherein the second transducer unit comprises a plurality of segments substantially aligned along the path of the signal;
   identifying a velocity at each segment in the plurality of segments for a number of modes for the signal to form identified velocities; and
   determining whether the inconsistency is present along the path through the object using the identified velocities for the number of modes for the signal and further determining whether a difference between the identified velocities is greater than a threshold, wherein the inconsistency is present along the path through the object when the difference is greater than the threshold.

2. The method of claim 1, wherein the number of modes comprises an asymmetric mode.

3. The method of claim 1, wherein the signal is a Lamb wave.

4. The method of claim 1, wherein the plurality of segments are transducers in the second transducer unit.

5. The method of claim 1, wherein the second transducer unit comprises a transducer and the segments are in the transducer.

6. The method of claim 1, wherein the path passes through a material in the object in which the material is selected from one of a composite material, a metal, titanium, aluminum, and steel.

7. The method of claim 1, wherein the object is selected from one of an aircraft, an airplane, a helicopter, a spacecraft, a space station, a satellite, a composite structure for the aircraft, a skin panel, an engine, a fuselage, a wing, a rib, and a stringer.

8. A health monitoring system comprising:
   a first transducer unit;
   a second transducer unit comprising a plurality of segments; and
   a signal analysis module configured to identify velocities for a number of modes for a signal sent from the first transducer unit and received at the plurality of segments of the second transducer unit, wherein the signal is sent along a path through an object from the first transducer unit to the second transducer unit, the plurality of segments substantially aligned along the path; and further configured to determine whether an inconsistency is present along the path through the object using identified velocities for the number of modes for the signal such that the signal analysis module is configured to determine whether a difference between the identified velocities is greater than a threshold, wherein the inconsistency is present along the path through the object when the difference is greater than the threshold.

9. The health monitoring system of claim 8 further comprising:
   a transducer system associated with the object, wherein the first transducer unit and the second transducer unit are part of the transducer system.

10. The health monitoring system of claim 8, wherein the signal is a Lamb wave.

11. The health monitoring system of claim 8, wherein the number of modes comprises an asymmetric mode.

12. The health monitoring system of claim 8, wherein the second transducer unit comprises a transducer and the plurality of segments are in the transducer.

13. A health monitoring system of an aircraft, the health monitoring system comprising:
   a transducer system associated with an object in the aircraft; and
   a signal analysis module configured to cause a first transducer unit in the transducer system to send a signal along a path in the object to a second transducer unit in the transducer system in which the second transducer unit has segments; identify a velocity for each segment for a number of modes for the signal to form identified velocities for the number of modes for the signal; and determine whether an inconsistency is present along the path through the object using the identified velocities for the number of modes for the signal, wherein the determining step comprises:
   determining whether a difference between the identified velocities is greater than a threshold, wherein the inconsistency is present along the path through the object when the difference is greater than the threshold.

14. The health monitoring system of claim 13, wherein the signal is a Lamb wave and wherein the number of modes comprises an asymmetric mode.

15. The health monitoring system of claim 13, wherein the segments are transducers in the second transducer unit and are substantially aligned along the path.

16. A method for operating a health monitoring system for an object, the method comprising:
   receiving a signal sent from a first transducer unit at a second transducer unit, wherein the signal is sent along a path through an object from the first transducer unit to the second transducer unit and wherein the second transducer unit comprises a plurality of segments substantially aligned along the path of the signal;
   identifying a velocity at each segment in the plurality of segments for a number of modes for the signal to form identified velocities; and
   determining whether a difference among the identified velocities at each segment is greater than a threshold.

17. The method of claim 16 further comprising generating an alert if a difference among the identified velocities is greater than the threshold.

* * * * *